(12) United States Patent
Schmainda et al.

(10) Patent No.: US 7,567,832 B2
(45) Date of Patent: Jul. 28, 2009

(54) MRI METHOD FOR MEASURING TUMOR HEMODYNAMIC PARAMETERS IN THE PRESENCE OF CONTRAST AGENT EXTRAVASATION

(75) Inventors: Kathleen M. Schmainda, Elm Grove, WI (US); Christopher Quarles, Milwaukee, WI (US); B. Douglas Ward, West Allis, WI (US)

(73) Assignee: The MCW Research Foundation, Milwaukee, WI (US)

( * ) Notice: Subject to any disclaimer, the term of this patent is extended or adjusted under 35 U.S.C. 154(b) by 582 days.

(21) Appl. No.: 11/202,997

(22) Filed: Aug. 12, 2005

(65) Prior Publication Data
US 2006/0034765 A1   Feb. 16, 2006

Related U.S. Application Data

(60) Provisional application No. 60/601,336, filed on Aug. 13, 2004.

(51) Int. Cl.
 *A61B 5/05* (2006.01)
(52) U.S. Cl. .............. 600/410; 600/419; 600/420; 324/306; 324/309
(58) Field of Classification Search .............. 600/419, 600/420; 324/306, 309
See application file for complete search history.

(56) References Cited

U.S. PATENT DOCUMENTS

| 5,799,649 | A | * | 9/1998 | Prince ............ 600/420 |
| 6,807,441 | B2 |  | 10/2004 | Schmainda |
| 7,069,068 | B1 | * | 6/2006 | Ostergaard ......... 600/420 |
| 2002/0026116 | A1 | * | 2/2002 | Schmainda ......... 600/419 |

OTHER PUBLICATIONS

C.C. Quarles, et al;Quantitative Cerebral Perfusion Imaging Using MRI: A Technical Perspective; ISMRM Syllabus, Mar. 21-23, 2004, Venice, Italy.

* cited by examiner

*Primary Examiner*—Long V Le
*Assistant Examiner*—Joel F Brutus
(74) *Attorney, Agent, or Firm*—Quarles & Brady LLP (57) ABSTRACT

One or two sets of time course NMR data are acquired using an EPI pulse sequence in which either or both gradient recalled echo NMR signals and spin-echo NMR signals are acquired after bolus injection of a contrast agent. $T_2^*$ relaxation rates for GE and $T_2$ relaxation rates for SE are calculated from the acquired NMR signals and are corrected for extravasation of contrast agent into surrounding tissues. The gradient-echo signals and spin-echo NMR signals are employed along with the $T_2^*$ and $T_2$ relaxation rates to calculate hemodynamic parameter maps which are used as a measure of tumor angiogenesis.

10 Claims, 4 Drawing Sheets

MRI METHOD FOR MEASURING TUMOR HEMODYNAMIC PARAMETERS IN THE PRESENCE OF CONTRAST AGENT EXTRAVASATION

CROSS-REFERENCE TO RELATED APPLICATIONS

This application claims the benefit of U.S. Provisional patent application Ser. No. 60/601,336 filed on Aug. 13, 2004 and entitled "Improving the Reliability Of Obtaining Tumor Hemodynamic Parameters In The Presence Of Contrast Agent Extravasation".

STATEMENT REGARDING FEDERALLY SPONSORED RESEARCH

This invention was made with government support under Grant No. ROI CA082500 awarded by the National Institute of Health. The United States Government has certain rights in this invention.

BACKGROUND OF THE INVENTION

The field of the invention is magnetic resonance imaging (MRI), and particularly, the imaging of tumors in the human brain and other parts of the body.

In the United States, approximately 17,000 new patients are diagnosed each year with a primary intracranial neoplasm. Approximately 60% of these tumors are malignant, and gliomas are the most common type. Although there is a wide variability in life expectancy for patients with the various subtypes of gliomas, their prognosis is generally poor. This is especially true for those with high-grade gliomas, in spite of treatment modalities such as surgery, radiation therapy and chemotherapy. The most aggressive gliomas are those characterized by angiogenesis, a process of new vessel growth essential for the progression of the tumor from low-grade to high-grade. There is also a clear correlation between increased vascularity of the tumor and increased malignancy. Given the vascular nature of these tumors and the lack of success with standard cancer treatments, there is both a great need and hope for therapies that inhibit angiogenesis. Now that several of these agents are entering clinical trials an assessment of their ability to inhibit angiogenesis is crucial to evaluating their clinical potential.

Contrast-enhanced conventional MRI methods have become the imaging standard for the depiction and detection of brain tumors. However, these post-contrast, steady-state methods do not provide reliable information about tumor angiogenesis. The tumor signal enhancement volume that is measured by these prior methods depends on the status of the blood-brain barrier, which is affected by both tumor type and prior treatments for the disease. In addition, a tumor's response to an anti-angiogenic therapy can occur before effects on tumor volume can be detected, or may even occur with increases in tumor volume that result from the evolution of local necroses. Finally, an anti-angiogenic therapy may be judged successful, not necessarily because it results in tumor shrinkage, but because it stabilizes the tumor or returns it to a dormant state. For these reasons, non-invasive methods that can more specifically monitor vessel growth and regression in tumors are needed for the evaluation of anti-angiogenic therapies.

Over the past decade, contrast agent based MRI methods, both relaxivity ($T_1$) and susceptibility ($T_2$, $T_2^*$)-weighted methods, have demonstrated the potential to measure many characteristics of tumor hemodynamics. The $T_1$ methods, commonly termed dynamic contrast enhanced (DCE) MRI, have been widely used for estimating the plasma-tissue contrast agent transfer constant, $K^{trans}$, and the extravascular extracellular space (EES). Of these, perhaps the most reliable parameter is $K^{trans}$, which has been shown to change during angiogenic therapy.

The $T_2$ or $T_2^*$ methods typically referred to as dynamic susceptibility contrast (DSC) MRI have been commonly used to measure tumor cerebral blood volume (CBV) and more recently the cerebral blood flow (CBF), and mean transit time (MTT). DSC derived tumor blood volume data have demonstrated a correlation with tumor grade. The MTT can be used as an indicator of perfusion efficiency and has been shown to be very heterogeneous in rat brain tumor models. Additionally, intravoxel transit time and flow distributions can be computed using DSC methods. These distributions are markers of flow heterogeneity and are useful in the evaluation of antiangiogenic therapies. They have shown great promise in predicting the final infarct size following acute stroke.

DSC methods rely on the compartmentalization of the contrast agent such that a susceptibility gradient can be induced between the contrast-containing compartment, which is typically the vasculature, and the extravascular space. A potential difficulty with DSC MRI methods to study tumors results from the fact that currently only small molecular weight Gadolinium (Gd) agents are available for clinical use. In normal brain tissue, for which the blood-brain-barrier (BBB) is intact, the passage of a bolus of a Gd agent through the tissue induces a susceptibility gradient that results in a signal reduction. However, when there is a disruption of the BBB, as is frequently the case with brain tumors, contrast agent leaks out of the vasculature into the tissue resulting in enhanced $T_1$ relaxation effects. Signal increases that result from shortening $T_1$ competes with the susceptibility-induced signal decreases. As expected, contrast agent leakage can lead to an underestimation of tumor blood volume and flow. In tissues outside of the brain, where no blood brain barrier exists, the Gd contrast agents always leak out of the vascular space. Thus, DSC methods have up until now been somewhat limited in their use outside of the brain.

Numerous techniques have been proposed to eliminate $T_1$ leakage effects including dual echo pulse sequences and model-based permeability compensation methods. The model-based leakage correction methods require no changes in pulse sequence design so that clinically available imaging sequences can be used to measure the dynamic signal changes following contrast administration.

A model-based correction approach is described in U.S. Pat. No. 6,807,441 to correct GE and SE CBV maps for contrast agent leakage. The corrected CBV demonstrated good success in the preliminary evaluation of brain tumors. In particular in a group of 15 patients, it was demonstrated that only when the leakage correction was applied did a statistically significant correlation result between tumor CBV and grade. However, this approach is limited to the calculation of CBV. In order to eliminate leakage effects on other tumor hemodynamic parameters, such as CBF (cerebral blood flow) and MTT (mean transit time), the original MR signal time course must also be corrected for leakage effects prior to their determination.

SUMMARY OF THE INVENTION

The present invention is an improved model-based leakage correction method that more precisely produces an NMR signal as would exist without contrast agent extravascular leakage. A time course image data set is acquired and either a T2 relaxation rate data set or $T_2^*$ relaxation rate data set is calculated therefrom which is corrected to take into account extravasation of contrast agent. An image of any one or more hemodynamic parameters may be calculated using the corrected T2 or T2* relaxation rate data set.

A general object of the invention is to more accurately assess the hemodynamic properties of a tumor where extravasation of contrast agent is present. The invention is particularly applicable to brain tumor assessment where the blood-brain barrier is disrupted due to disease. However, the present invention also is applicable to assessment of tumors in other parts of the human body where extravasation is inherently present.

GENERAL DESCRIPTION OF THE INVENTION

A detailed model for the MR signal in terms of the dominant $T_1$ and $T_2$ (or $T_2^*$) effects of a Gadolinium contrast agent (Gd) is well known. Briefly, the measured or effective $\Delta R2^*$ time curve can be written in terms of the combined $T_2^*$ and $T_1$-dominated effects:

$$\Delta R2^*_{meas}(t) = \overbrace{\Delta R2^*_{tumor}(t)}^{T2^* \text{ term}} - \overbrace{\frac{TR}{TE} \frac{\exp(-TR/T_1)}{(1-\exp(-TR/T_1))} R_1 C_t(t)}^{T1 \text{ term}}, \quad (1)$$

where $\Delta R2^*_{tumor}(t)$ is the tumor $\Delta R2^*(t)$ as would exist without leakage, $R_1$ is the $T_1$ relaxivity, $C_t(t)$ is the tissue contrast agent concentration, TE is the pulse sequence echo time, TR is the repetition time, and $\Delta R2^*_{meas}(t)$ is determined from the natural logarithm of the ratio of the measured pre- and post-contrast signal, which may be affected by leakage:

$$\Delta R2^*_{meas}(t) = \frac{-1}{TE} \log\left(\frac{S(t)_{post}}{S_{pre}}\right). \quad (2)$$

Assuming there is no back diffusion of Gd from the tissue space to the vascular space, the tissue Gd concentration can be expressed as:

$$\frac{dC_t(t)}{dt} = PS \cdot C_c(t) = k\Delta R2^*_{tumor}(t), \quad (3)$$

where PS is the permeability-surface area product, $C_c(t)$ is the vascular concentration of Gd, and k is the product of PS (the contrast agent calibration factor) and the fractional blood volume. Integration of equation (3) and substitution for $C_t(t)$ into equation (1) gives:

$$\Delta R2^*_{meas}(t) = \Delta R2^g_{tumor}(t) - \frac{TR}{TE} \frac{\exp(-TR/T_1)}{(1-\exp(-TR/T_1))} R_1 k \int_0^t \Delta R2^*_{tumor}(\tau)d\tau \quad (4)$$

Since $\Delta R2^*_{tumor}(t)$ cannot be directly measured in the presence of leakage we have to estimate it using some function $\Delta R2^*_{est}(t)$. Equation (4) can be then be rewritten in terms of the $T_2^*$ and $T_1$ dominant factors, each given as a function of $\Delta R2^*_{est}(t)$:

$$\Delta R2^*_{meas}(t) \approx \overbrace{K1\Delta R2^*_{est}(t)}^{T2^* \text{ term}} - \overbrace{K2 \int_0^t \Delta R2^*_{est}(\tau)d\tau}^{T1 \text{ term}}, \quad (5)$$

where K1 and K2 are the susceptibility and permeability weighting factors as previously defined. In the correction method described in U.S. Pat. No. 6,807,441, $\Delta R2^*_{est}(t)$ was set equal to the average healthy tissue $\Delta R2^*(t)$. Thus it is assumed that a leaky tumor $\Delta R2^*(t)$ can be modeled as a scaled version of a $\Delta R2^*(t)$ from healthy tissue. Given that tumor hemodynamics are extremely heterogeneous both across and within the same tumor, this is probably not a good assumption. Thus, we hypothesize that an improved estimate must allow for this heterogeneity.

To better estimate $\Delta R2^*_{tumor}(t)$ an approach is used to model $\Delta R2^*_{meas}(t)$ that is based on the tracer dilution theory typically used to compute the vascular residue function and CBF. It has been previously shown that the passage of contrast agent through a given volume of interest VOI, $C_{VOI}(t)$, can be expressed as the convolution of the arterial input function (AIF or $C_a(t)$) with the residue function, R(t), which describes the fraction of injected contrast agent still present in the vasculature at time t:

$$C_{VOI}(t) = CBF \int_0^t C_a(\tau)R(t-\tau)d\tau. \quad (6)$$

Thus, the first step of our approach sets $\Delta R2^*_{est}(t)$ in the $T_2^*$ term of equation (5) equal to this definition of $C_{VOI}(t)$. The advantage of estimating $\Delta R2^*_{tumor}(t)$ using this definition is that the model estimates the underlying tumor tissue residue function for every voxel and does not assume a single function as in prior leakage correction methods.

We then set $\Delta R2^*_{est}(t)$ in the $T_1$ term of equation (5) equal to the AIF:

$$\Delta R2^*_{meas}(x,y,t) \approx \overbrace{\beta_1 \int_0^t C_a(\tau)R(x,y,t-\tau)d\tau}^{T2^* \text{ term}} - \overbrace{\beta_2 \int_0^t C_a(\tau)d\tau}^{T1 \text{ term}}, \quad (7)$$

where $\beta_1$ and $\beta_2$ are initial estimates of the susceptibility and permeability weighting factors (K1 and K2) and the x and y coordinates are included to reflect the per-voxel, imaging nature of this approach. After some time, T, all the contrast agent in the vasculature will flow out of the voxel making R(t)=0. Also, before the contrast agent is injected the AIF will be 0. Thus, equation (7) becomes:

$$\Delta R2^*_{meas}(x, y, t) \approx \beta_1 \int_0^t C_a(t-\tau)R(x, y, \tau)d\tau - \beta_2 \int_0^t C_a(\tau)d\tau, \quad (8)$$

under the conditions R(t)=0 for t>T and $C_a(t-\tau)$=0 for $\tau$>t.

R(x,y,t) can be computed using the same SVD deconvolution approach described in by Ostergaard L, Sorensen A, Kwong W, Weiskoff R, Glydensted C, Rosen B, "High Resolution Measurement Of Cerebral Blood Flow Using Intravascular Tracer Bolus Passages. Part I: Mathematical Approach And Statistical Analysis", Magn. Reson. Med. 2000; 36: 175-725. However, the matrix notation originally described must be rewritten to include the $T_1$ term:

$$\Delta R2^*_{meas}(t_n) \approx \Delta t \sum_{i=0}^{M} C_a(t_{n-i})R'(t_i) + \beta_2 I_a(t_n) \quad (9)$$

or $$\begin{pmatrix} \Delta R2^*_{meas}(t_1) \\ \Delta R2^*_{meas}(t_2) \\ \vdots \\ \Delta R2^*_{meas}(t_M) \\ \vdots \\ \Delta R2^*_{meas}(t_N) \end{pmatrix} = \Delta t \begin{pmatrix} C_a(t_1) & 0 & \cdots & 0 & I_a(t_1) \\ C_a(t_2) & C_a(t_1) & \cdots & 0 & I_a(t_2) \\ \vdots & \vdots & \ddots & \vdots & \vdots \\ C_a(t_M) & \cdots & \cdots & C_a(t_1) & I_a(t_M) \\ \vdots & \vdots & \vdots & \vdots & \vdots \\ C_a(t_N) & C_a(t_{N-1}) & \cdots & C_a(t_{N-M}) & I_a(t_N) \end{pmatrix} \begin{pmatrix} R'(T_1) \\ R'(T_2) \\ \vdots \\ R'(T_M) \\ \beta_2 \end{pmatrix} \quad (10)$$

where $R'(t_i) \approx \beta_1 R(t)$, $I_a(t_n)$ is the cumulative sum of the AIF, N is the number of data points used for the fit, $t_1$ is equal to the start of the AIF, and M is the end of the AIF. To avoid multi-collinearity N must be greater than M which is reasonable because the permeability effects have a longer duration than that of R(t).

We can now redefine $\Delta R2^*_{est}(t)$ as the convolution of the AIF and the computed residue function in equation (8):

$$\Delta R2^*_{est}(x, y, t) = \int_0^t C_a(t-\tau)R'(x, y, \tau)d\tau. \quad (11)$$

The next step is to substitute our new $\Delta R2^*_{est}(t)$ into equation (5) and estimate the weighting factors K1 and K2 using a simple linear least squares fit. The corrected $\Delta R2^*(t)$ can then be written as:

$$\Delta R2^*_{corr}(x,y,t) = \Delta R2^*_{meas}(x,y,t) + K2(x,y) \int_0^t \Delta R2^*_{est}(x,y,\tau)d\tau. \quad (12)$$

The $\Delta R2^*_{corr}(t)$ can then be used to calculate the tumor hemodynamic parameters.

DETAILED DESCRIPTION OF THE PREFERRED EMBODIMENT

Figure 1:
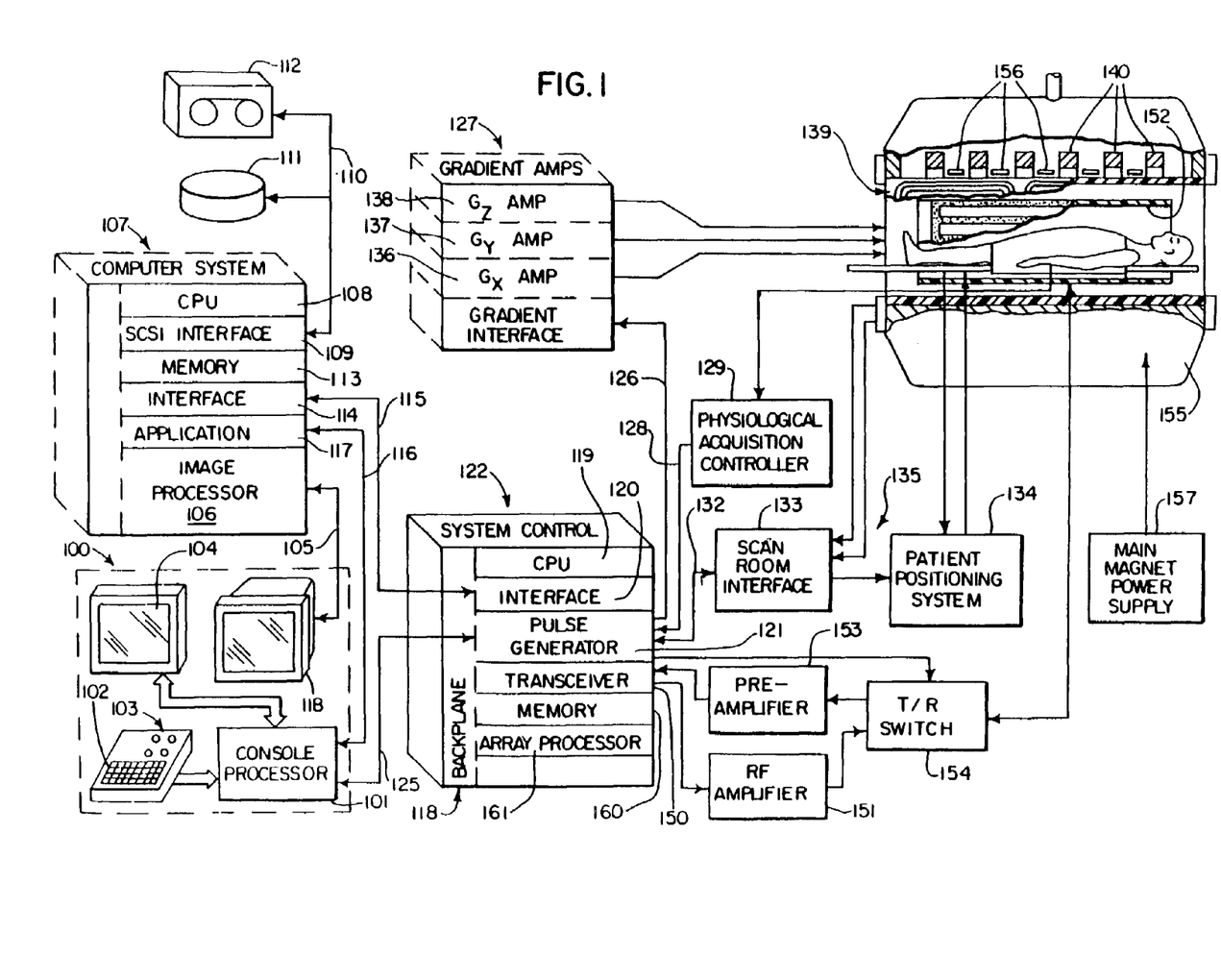
FIG. 1 is a block diagram of an MRI system used to acquire NMR data according to a preferred embodiment of the invention.

Referring first to FIG. 1, there is shown the major components of a preferred NMR system which incorporates the present invention and which is sold by the General Electric Company under the trademark "SIGNA". The operation of the system is controlled from an operator console 100 which includes a console processor 101 that scans a keyboard 102 and receives inputs from a human operator through a control panel 103 and a plasma display/touch screen 104. The console processor 101 communicates through a communications link 116 with an applications interface module 117 in a separate computer system 107. Through the keyboard 102 and controls 103, an operator controls the production and display of images by an image processor 106 in the computer system 107, which connects directly to a video display 118 on the console 100 through a video cable 105.

The computer system 107 is formed about a backplane bus which conforms with the VME standards, and it includes a number of modules which communicate with each other through this backplane. In addition to the application interface 117 and the image processor 106, these include a CPU module 108 that controls the VME backplane, and an SCSI interface module 109 that connects the computer system 107 through a bus 110 to a set of peripheral devices, including disk storage 111 and tape drive 112. The computer system 107 also includes a memory module 113, known in the art as a frame buffer for storing image data arrays, and a serial interface module 114 that links the computer system 107 through a high speed serial link 115 to a system interface module 120 located in a separate system control cabinet 122.

The system control 122 includes a series of modules which are connected together by a common backplane 118. The backplane 118 is comprised of a number of bus structures, including a bus structure which is controlled by a CPU module 119. The serial interface module 120 connects this backplane 118 to the high speed serial link 115, and pulse generator module 121 connects the backplane 118 to the operator console 100 through a serial link 125. It is through this link 125 that the system control 122 receives commands from the operator which indicate the scan sequence that is to be performed.

The pulse generator module 121 operates the system components to carry out the desired scan sequence. It produces data which indicates the timing, strength and shape of the RF pulses which are to be produced, and the timing of and length of the data acquisition window. The pulse generator module 121 also connects through serial link 126 to a set of gradient amplifiers 127, and it conveys data thereto which indicates the timing and shape of the gradient pulses that are to be produced during the scan. The pulse generator module 121 also receives patient data through a serial link 128 from a physiological acquisition controller 129. The physiological acquisition control 129 can receive a signal from a number of different sensors connected to the patient. For example, it may receive ECG signals from electrodes or respiratory signals from a bellows and produce pulses for the pulse generator module 121 that synchronizes the scan with the patient's cardiac cycle or respiratory cycle. And finally, the pulse generator module 121 connects through a serial link 132 to scan room interface circuit 133 which receives signals at inputs 135 from various sensors associated with the position and condition of the patient and the magnet system. It is also through the scan room interface circuit 133 that a patient positioning system 134 receives commands which move the patient cradle and transport the patient to the desired position for the scan.

The gradient waveforms produced by the pulse generator module 121 are applied to a gradient amplifier system 127 comprised of $G_x$, $G_y$ and $G_z$ amplifiers 136, 137 and 138, respectively. Each amplifier 136, 137 and 138 is utilized to excite a corresponding gradient coil in an assembly generally designated 139. The gradient coil assembly 139 forms part of a magnet assembly 155 which includes a polarizing magnet 140 that produces a 1.5 Tesla polarizing field that extends horizontally through a bore. The gradient coils 139 encircle the bore, and when energized, they generate magnetic fields In the same direction as the main polarizing magnetic field, but with gradients $G_x$, $G_y$ and $G_z$ directed in the orthogonal x-, y- and z-axis directions of a Cartesian coordinate system. That is, if the magnetic field generated by the main magnet 140 is directed in the z direction and is termed BO, and the total magnetic field in the z direction is referred to as $B_z$, then $G_x = \partial B_z/\partial x$, $G_y = \partial B_z/\partial y$ and $G_z = \partial B_z/\partial z$, and the magnetic field at any point (x,y,z) in the bore of the magnet assembly 141 is given by $B(x,y,z) = B_o + G_x x + G_y y G_z z$. The gradient magnetic fields are utilized to encode spatial information into the NMR signals emanating from the patient being scanned. Because the gradient fields are switched at a very high speed when an EPI sequence is used to practice the preferred embodiment of the invention, local gradient coils are employed in place of the whole-body gradient coils 139. These local gradient coils are designed for the head and are in close proximity thereto. This enables the inductance of the local gradient coils to be reduced and the gradient switching rates increased as required for the EPI pulse sequence. For a description of these local gradient coils which is incorporated herein by reference, see U.S. Pat. No. 5,372,137 issued on Dec. 13, 1994 and entitled "NMR Local Coil For Brain Imaging".

Located within the bore 142 is a circular cylindrical whole-body RF coil 152. This coil 152 produces a circularly polarized RF field in response to RF pulses provided by a transceiver module 150 in the system control cabinet 122. These pulses are amplified by an RF amplifier 151 and coupled to the RF coil 152 by a transmit/receive switch 154 which forms an integral part of the RF coil assembly. Waveforms and control signals are provided by the pulse generator module 121 and utilized by the transceiver module 150 for RF carrier modulation and mode control. The resulting NMR signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150.

The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate local RF head coil to be used in the transmit and receive mode to improve the signal-to-noise ratio of the received NMR signals. With currently available NMR systems such a local RF coil is preferred in order to detect small variations in NMR signal. Reference is made to the above cited U.S. Pat. No. 5,372,137 for a description of the preferred local RF coil.

In addition to supporting the polarizing magnet 140 and the gradient coils 139 and RF coil 152, the main magnet assembly 141 also supports a set of shim coils 156 associated with the main magnet 140 and used to correct inhomogeneities in the polarizing magnet field. The main power supply 157 is utilized to bring the polarizing field produced by the superconductive main magnet 140 to the proper operating strength and is then removed.

The NMR signals picked up by the RF coil are digitized by the transceiver module 150 and transferred to a memory module 160 which is also part of the system control 122. When the scan is completed and an entire array of data has been acquired in the memory modules 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the video display 118 as will be described in more detail hereinafter.

Figure 2:
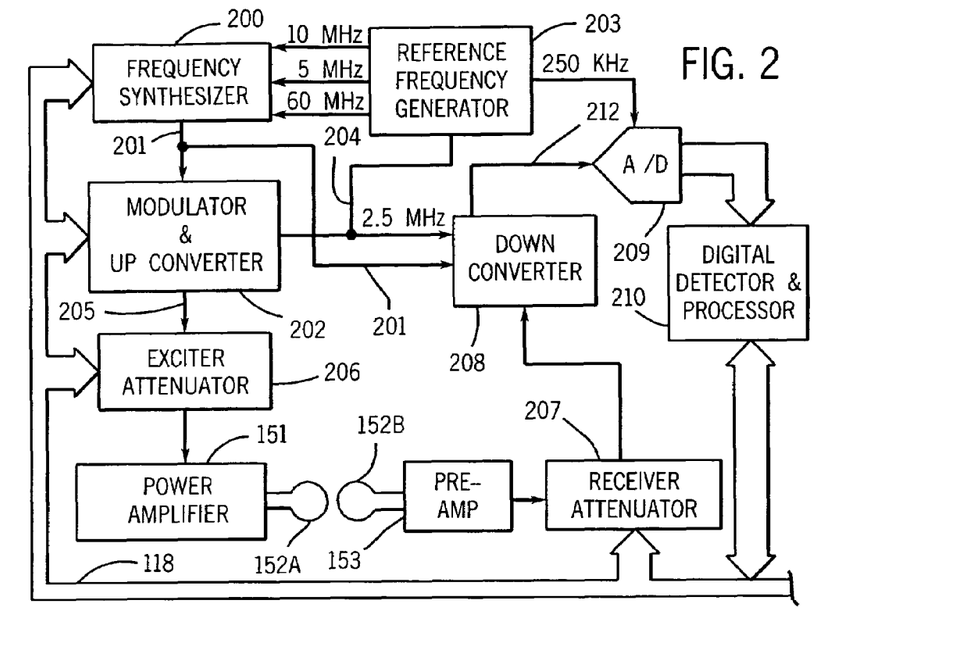
FIG. 2 is a block diagram of a transceiver which forms part of the MRI system of FIG. 1.

Referring particularly to FIGS. 1 and 2, the transceiver 150 includes components which produce the RF excitation field B1 through power amplifier 151 at a coil 152A and components which receive the resulting NMR signal induced in a coil 152B. As indicated above, the coils 152A and B may be a single whole-body coil, but the best results are achieved with a single local RF coil specially designed for the head. The base, or carrier, frequency of the RF excitation field is produced under control of a frequency synthesizer 200 which receives a set of digital signals (CF) through the backplane 118 from the CPU module 119 and pulse generator module 121. These digital signals indicate the frequency and phase of the RF carrier signal which is produced at an output 201. The commanded RF carrier is applied to a modulator and up converter 202 where its amplitude is modulated in response to a signal R(t) also received through the backplane 118 from the pulse generator module 121. The signal R(t) defines the envelope, and therefore the bandwidth, of the RF excitation pulse to be produced. It is produced in the module 121 by sequentially reading out a series of stored digital values that represent the; desired envelope. These stored digital values may, in turn, be changed from the operator console 100 to enable any desired RF pulse envelope to be produced. The modulator and up converter 202 produces an RF pulse at the desired Larmor frequency at an output 205. The magnitude of the RF excitation pulse output through line 205 is attenuated by an exciter attenuator circuit 206 which receives a digital command, TA, from the backplane 118. The attenuated RF excitation pulses are applied to the power amplifier 151 that drives the RF coil 152A. For a more detailed description of this portion of the transceiver 122, reference is made to U.S. Pat. No. 4,952,877 which is incorporated herein by reference.

Referring still to FIGS. 1 and 2 the NMR signal produced by the subject is picked up by the receiver coil 152B and applied through the preamplifier 153 to the input of a receiver attenuator 207. The receiver attenuator 207 further amplifies the NMR signal and this is attenuated by an amount determined by a digital attenuation signal (RA) received from the backplane 118. The receive attenuator 207 is also turned on and off by a signal from the pulse generator module 121 such that it is not overloaded during RF excitation. The received NMR signal is at or around the Larmor frequency, which in the preferred embodiment is around 63.86 MHz for 1.5 Tesla. This high frequency signal is down converted in a two step process by a down converter 208 which first mixes the NMR signal with the carrier signal on line 201 and then mixes the resulting difference signal with the 2.5 MHz reference signal on line 204. The resulting down converted NMR signal on line 212 has a maximum bandwidth of 125 kHz and it is centered at a frequency of 187.5 kHz. The down converted NMR signal is applied to the input of an analog-to-digital (A/D) converter 209 which samples and digitizes the analog signal at a rate of 250 kHz. The output of the A/D converter 209 is applied to a digital detector and signal processor 210 which produce 16-bit in-phase (I) values and 16-bit quadrature (Q) values corresponding to the received digital signal. The resulting stream of digitized I and Q values of the received NMR signal is output through backplane 118 to the memory module 160 where they are employed to reconstruct an image.

To preserve the phase information contained in the received NMR signal, both the modulator and up converter 202 in the exciter section and the down converter 208 in the receiver section are operated with common signals. More particularly, the carrier signal at the output 201 of the frequency synthesizer 200 and the 2.5 MHz reference signal at the output 204 of the reference frequency generator 203 are employed in both frequency conversion processes. Phase consistency is thus maintained and phase changes in the detected NMR signal accurately indicate phase changes produced by the excited spins. The 2.5 MHz reference signal as well as 5, 10 and 60 MHz reference signals are produced by the reference frequency generator 203 from a common 20 MHz master clock signal. The latter three reference signals are employed by the frequency synthesizer 200 to produce the carrier signal on output 201. For a more detailed description of the receiver, reference is made to U.S. Pat. No. 4,992,736 which is incorporated herein by reference.

Figure 3:
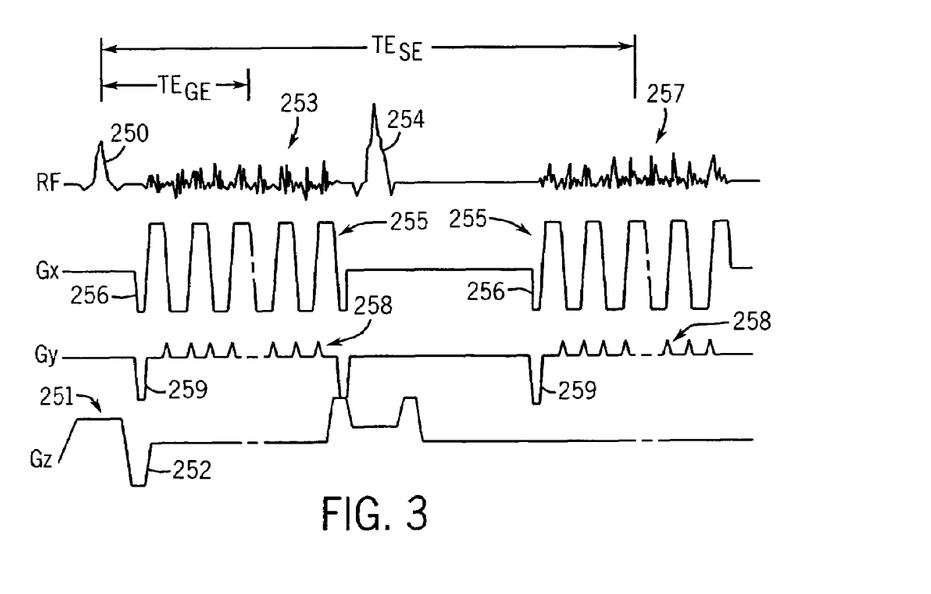
FIG. 3 is a graphic illustration of a preferred pulse sequence performed by the MRI system of FIG. 1.

The EPI pulse sequence employed in the preferred embodiment of the invention is illustrated in FIG. 3. A 90° RF excitation pulse 250 is applied in the presence of a Gz slice select gradient pulse 251 to produce transverse magnetization in a slice through the brain. The excited spins are rephased by a negative lobe 252 on the slice select gradient Gz and then a time interval elapses before the readout sequence begins. A total of 64 separate NMR gradient recalled echo signals, indicated generally at 253, are acquired during the first part of the readout sequence. Each NMR gradient-recalled echo signal 253 is a different view which is separately phase encoded to scan $k_y$-space from $k_y=-32$ to $k_y=+32$ in monotonic order. The readout sequence is positioned such that the view acquired at $k_y=0$ occurs at the desired echo time $TE_{GE}$. The NMR signals 253 are referred to hereinafter as the GE NMR signals 253.

Following the readout of the GE NMR signals 253 a 180° RF refocusing pulse 254 is applied to invert the transverse spin magnetization and cause it to refocus at a second desired echo time $TE_{SE}$. A total of 64 separate NMR spin echo signals, indicated generally at 257, are acquired during this second part of the readout sequence. Each NMR spin echo signal 257 is a different view which is separately phase encoded to scan ky-space from ky=−32 to ky=+32 in monotonic order. The readout sequence is positioned such that the view acquired at ky=0 occurs at the desired spin echo time $TE_{SE}$. The NMR spin echo signals 257 are referred to hereinafter as the SE NMR signals 257.

The NMR echo signals 253 and 257 are acquired in the presence of an oscillating $G_x$ readout gradient field 255. Each readout sequence is started with a negative readout gradient lobe 256 and the echo signals 253 and 257 are produced as the readout gradient 255 oscillates between positive and negative values. A total of 64 samples are taken of each NMR echo signal 253 or 257 during each readout gradient pulse 255. The successive NMR echo signals 253 and 257 are separately phase encoded by a series of $G_y$ phase encoding gradient pulses 258. The first gradient pulse is a negative lobe 259 that occurs before the echo signals are acquired to encode the first view at $k_y=-32$. Subsequent phase encoding pulses 258 occur as the readout gradient pulses 255 switch polarity, and they step the phase encoding monotonically upward through $k_y$ space.

At the completion of the EPI pulse sequence, therefore, 64 separate frequency encoded samples of 64 separately phase encoded GE NMR signals 253 and SE NMR signals 257 have been acquired. Each 64×64 element arrays of complex numbers is Fourier transformed along both of its dimensions ($k_y$ and $k_x$) to produce a 64×64 element array of image data that indicates the NMR signal magnitude along each of its two dimensions (y and x). As explained above, a two dimensional Fourier transformation is performed by the array processor 161 (FIG. 1) and each resulting NMR image data set is stored in the disk 111 for further processing by the image processor 106 according to the present invention. These two images are referred to hereinafter as $I_{GE}$ and $I_{SE}$, and the magnitude of the signals at each of their respective pixels is referred to as $S_{GE}$ and $S_{SE}$.

While the pulse sequence of FIG. 3 is preferred, the present invention may be employed with many different pulse sequences, such as a gradient-echo EPI pulse sequence or a spin-echo EPI pulse sequence. The choice will usually depend on what pulse sequences are available on the MRI system being used and the particular hemodynamic parameters that are to be mapped.

Figure 4:
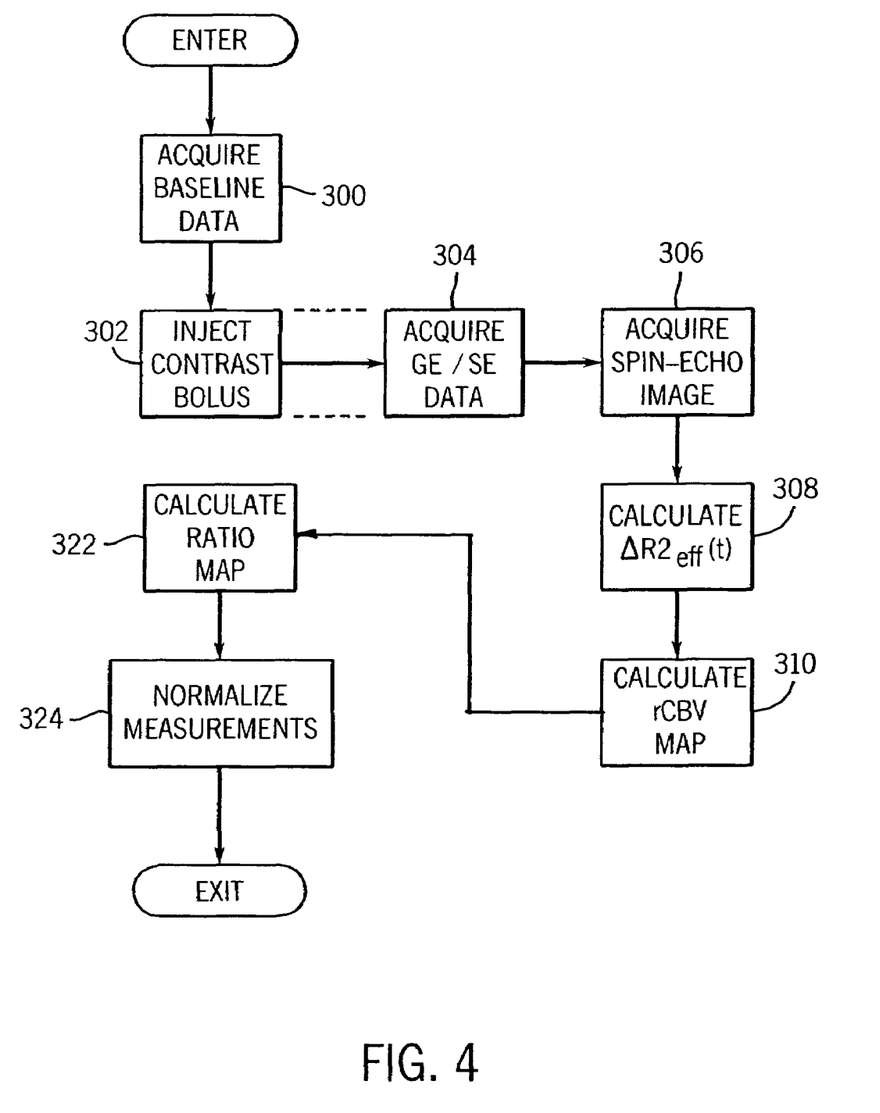
FIG. 4 is a flow chart of a preferred method for practicing the present invention using the MRI sequence of FIG. 1 and the pulse sequence of FIG. 3.

Referring particularly to FIG. 4, a dynamic study is conducted in which NMR data is acquired using the EPI pulse sequence of FIG. 3. Just prior to the dynamic imaging study, a 0.05 mmole/kg dose of Gadodiamide (Omniscan; Nycomed Amersham, Princeton N.J.) may be administered to the patient to diminish T1 effects that might result from agent extravasation. If the initial tissue T1 is decreased with contrast agent, subsequent changes in T1, which might occur during the first-pass study, are minimized. An acquisition using the pulse sequence of FIG. 3 is then performed. During the first minute of this acquisition simultaneous GE/SE are acquired as indicated at process block 300. These serve as baseline images. A 0.15-0.25 mmole/kg bolus injection of contrast agent is administered as indicated at process block 302, and the acquisition of data continues using the pulse sequence of FIG. 3 for 1 to 2 minutes as indicated at process block 304. Approximately 5 to 75 mm thick slices are acquired at $TE_{GE}$=30 ms and $TE_{SE}$=10 ms with fat suppression, a TR=1 s to 1.5 s and a FOV=24 cm. Finally, conventional post-contrast T1-weighted images of the same slices are acquired with a spin-echo pulse sequence (SE, TE/TR=11 ms/500 ms, matrix=256×256, NEX=2) as indicated at process block 306.

The gradient echo and spin echo data are reconstructed into images $I_{GE}$ and $I_{SE}$ and divided into two sets of time course data for each image slice. As will now be described, rCBV maps (corrected for agent extravasation), permeability-weighting (K2) maps, and transverse relaxation rate change ratio (ΔR2*/ΔR2) maps are created from these time course data sets. In addition, maps of other hemodynamic parameters, such as cerebral blood flow (CBF) and mean transit time (MTT) can also be calculated from this same data.

As indicated at process block 308, the effective change in the T2* relaxation rate $\Delta R2^*_{eff}(t)$ in the images $I_{GE}$ is determined for each image pixel at each time point in the time course data set. As will be described in more detail below with respect to FIG. 5, the present invention is a method for calculating this T2* relaxation rate which takes into account the extravasation of contrast agent. The same calculations may be repeated using the $I_{SE}$ images to calculate the T2 relaxation rate $\Delta R2_{eff}(t)$. This more accurate calculation enables the various hemodynamic parameter maps to be produced with far greater accuracy than in the past.

As indicated at process block 310, integration of the $\Delta R2^*_{eff}(t)$ values over the interval from 70 to 120 seconds during the time course study gives relative cerebral blood volume (rCBV) maps. These rCBV maps are corrected for leakage effects by virtue of the improved $\Delta R2^*_{eff}(t)$ computed according to the present invention. It should be apparent that these calculations can be done with either the $I_{GE}$ or $I_{SE}$ data, or with both of them to produce $rCBV_{SE}$ and $rCBV_{GE}$ maps.

Ratio maps are calculated using the $\Delta R2^*$ and $\Delta R2$ images as indicated at process block 322. The $T_2$ relaxation rate images ($\Delta R2^*$) are calculated using the series of time course images reconstructed from acquired gradient-echo NMR signals. The transverse relaxation rate change images ($\Delta R2$) are calculated with the series of images reconstructed from the acquired spin-echo NMR signals. Each pixel in a ratio map is calculated by averaging the ratios $\Delta R2^*/\Delta R2$ from corresponding pixels in ten images. The ten $T_2$ relaxation rate images are selected to encompass those produced from data acquired when blood contrast was at a maximum level after contrast bolus arrival. In the preferred embodiment this is detected by searching for the peak in the $\Delta R2^*$ values during the time course study.

Although all of the maps contain information regarding the imaged tumor, the corrected $rCBV_{GE}$ and corrected $rCBV_{SE}$ maps and the ratio map $\Delta R2^*/\Delta R2$ provide strong correlations with the tumor grade, which has been shown to correlate strongly with angiogenesis. Specifically, a strong statistical correlation was found between these MRI-derived measurements and the histopathologic tumor grade as determined with the Spearman rank correlation test, using p=0.05 as the significance threshold. To produce these measurements the data in respective $rCBV_{GE}$, $\Delta R2^*/\Delta R2$ and $rCBV_{SE}$ maps were extracted from ROIs placed both within the tumor, and contralateral brain, or normal-appearing white matter. When delineating the tumor ROI, care was taken to avoid any obviously necrotic areas as apparent on the post-contrast, high-resolution, T1-weighting images that were acquired. The corrected tumor rCBV measurement and the ratio measurement results are presented as normalized to corresponding contralateral brain measurements as indicated at process block 324.

Figure 5:
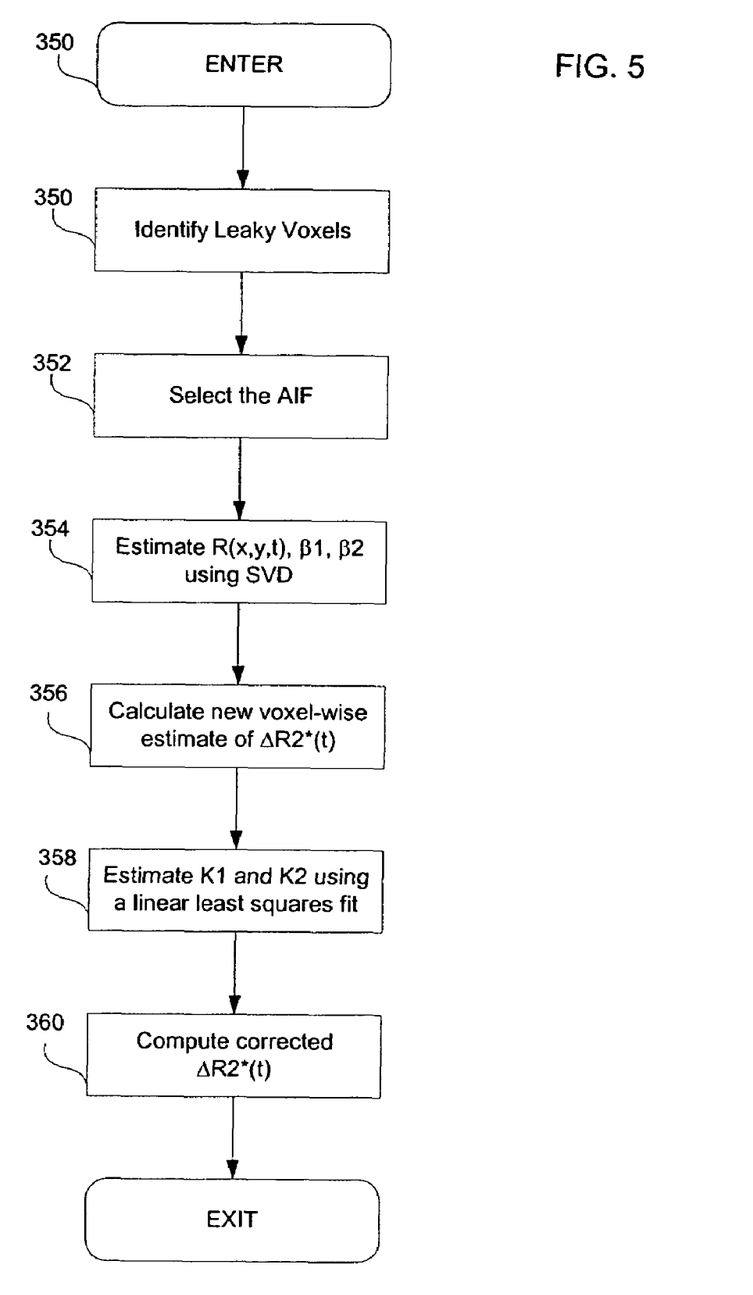
FIG. 5 is a flow chart of a preferred method for calculating corrected $T_2$ relaxation rate images which forms part of the method of FIG. 4.

The steps used in the preferred method for calculating the corrected $T_2$ relaxation rate images described above with reference to process block 308 is shown in more detail in FIG. 5. The first step indicated by process block 350 is to identify those voxels in the region of interest that demonstrate contrast agent extravasation. This is done by examining the magnitude of the time course NMR signal produced by each voxel and identifying those in which the signal near the end of this time course increases above a preselected threshold level. In the preferred embodiment a threshold of 3 standard deviations above the noise level is selected Next, as indicated at process block 352, NMR signals indicative of the arterial input function (AIF) are identified. This can be done manually by selecting 2 or 3 voxels located in an artery supplying the region of interest with blood. Automatic means may also employed to perform this step such as the method described in U.S. Pat. No. 6,546,275 entitled "Determination Of The Arterial Input Function In Dynamic Contrast Enhanced MRI" which is incorporated herein by reference.

The residue function R (x,y,t), the susceptibility weighting factor $\beta_1$ and the permeability weighting factor $\beta_2$ are calculated next as indicated at process block 354. This is an estimation given by the above-described equation (9) and, using the computed residual function and the AIF identified in process blocks 350 and 352. In the preferred embodiment a singular value deconvolution is employed to perform the matrix inversions needed to calculate the unknowns in this equation. A new estimate of the $T_2$ relaxation rate image ($\Delta R2^*_{est}(x,y,t)$) is then calculated as indicated at process block 356 using the above-described equation (11). This is the convolution of the AIF and the computed residue function R(x,y,t). The values of the weighting factors K1 and K2 can now be calculated as indicated at process block 358 by substituting the computed $T_2$ relaxation rate image ($\Delta R2^*_{corr}(x,y,t)$) into the above equation (5) and performing a least squares fit.

And finally, as indicated by process block 360, the corrected $T_2$ relaxation rate image ($\Delta R2^*_{corr}(x,y,t)$) is calculated. This is done using the above described equation (12), the calculated weighing factor K2 and the estimated $T_2$ relaxation rate image ($\Delta R2^*(x,y,t)$). From this corrected time course other hemodynamic values such as rCBV, CBF and MTT can be calculated.

Noninvasive methods by which tumor vasculature can be evaluated are crucial for establishing clinical endpoints related to angiogenesis and the therapeutic efficacy of its inhibitors. Given that the progression of tumors from low grade to high grade is angiogenesis-dependent, with a clear correlation between increased vascularity and increased malignancy, these results support the hypothesis that the acquired NMR information, derived with the methods described above, provide a measurement of both tumor angiogenesis and the efficacy of anti-angiogenic therapies. The corrected $rCBV_{GE}$ and $rCBV_{SE}$ measurements which reflect vessels of all sizes, and the $\Delta R2^*/\Delta R2$ ratio measurement are strongly associated with brain tumor grade.

While the present invention is particularly suited to imaging the human brain and diagnosing brain tumors, the invention may also be used to image tumors in other parts of the body. Hemodynamic parameters have previously been measured in brain tumors because the blood-brain barrier substantially inhibits extravascular leakage in many clinical cases. The present invention enables these hemodynamic parameters to be calculated even when there is extravascular leakage in the brain. It is clinically useful for brain tumor assessment when leakage is present and it is clinically useful in other parts of the body where extravascular leakage is inherently present.

We claim:

1. A method for producing an image of hemodynamic parameter with a magnetic resonance imaging (MRI) system, the steps comprising:
   a) injecting a contrast agent which alters the $T_1$ relaxation constant in tissues in a volume of interest;
   b) acquiring a time course image data set using the MRI system during the first passage of the contrast agent through the volume of interest;
   c) calculating from the time course image data set a T2 relaxation rate data set that is corrected to take into account extravasation of contrast agent into surrounding tissues; and
   d) producing an image of a hemodynamic parameter using the calculated T2 relaxation rate data set.

2. The method as recited in claim 1 in which step c) includes:
   c) i) determining an arterial input function for the volume of interest;
   c) ii) calculating a contrast agent residue function from the acquired time course image data set and the arterial input function; and c) iii) Producing the corrected T2 relaxation rate data set by calculating the convolution of the arterial input function and this calculated contrast agent residue function.

3. The method as recited in claim 2 in which step c) ii) is accomplished using a singular value deconvolution method.

4. A method for producing an image of a tumor in a patient's brain using a magnetic resonance imaging (MRI) system, the steps comprising:
   a) injecting a contrast agent which alters the $T_1$ relaxation constant in blood flowing through the patient's brain;
   b) acquiring two time course image data sets using the MRI system during the first passage of the contrast agent through the patient's brain with a pulse sequence in which gradient-recalled NMR signals are acquired to form one time course image data set, and in which spin-echo NMR signals are acquired to form a second time course image data set;
   c) calculating a set of T2* relaxation rate images from the one time course image data set that is corrected to take into account extravasation of contrast agent into surrounding tissues;
   d) calculating a set of $T_2$ relaxation rate images from the second time course image data set that is corrected to take into account extravasation of contrast agent into surrounding tissues; and
   e) calculating a ratio image by averaging the ratios of corresponding values in the set of T2* relaxation rate images and the set of $T_2$ relaxation rate images.

5. The method as recited in claim 4 in which the pulse sequence is an echo-planar imaging pulse sequence.

6. The method as recited in claim 4 which includes determining an arterial input function and steps c) and d) include calculating a contrast agent residue function from the acquired time course image data set and the arterial input function; and
   calculating the convolution of the arterial input function and the calculated contrast agent residue function.

7. The method as recited in claim 6 in which the contrast agent residue function is calculated using a singular value deconvolution method.

8. A method for assessing tumor angiogenesis which comprises:
   a) injecting a contrast agent which flows into the tumor to alter the $T_1$ relaxation constant in blood flowing through the tumor;
   b) acquiring two time course image data sets using a magnetic resonance imaging system during the first passage of the contrast agent through the tumor, one of the time course image data sets being acquired with a gradient-echo pulse sequence and the other one of the time course image data sets being acquired with a spin-echo pulse sequence;
   c) calculating a set of T2* relaxation rate images from the one time course image data set that is corrected to take into account extravasation of contrast agent into surrounding tissues;
   d) calculating a set of $T_2$ relaxation rate images from the second time course image data set that is corrected to take into account extravasation of contrast agent into surrounding tissues; and
   e) producing a $T_2$ relaxation rate ratio image by averaging the ratios of corresponding values in the set of T2* relaxation rate images and the set of $T_2$ relaxation rate images.

9. The method as recited in claim 8 which includes producing relative cerebral blood volume images ($rCBV_{GE}$ and $rCBV_{SE}$) using the respective two time course image data sets.

10. The method as recited in claim 8 which includes determining an arterial input function and steps c) and d) include calculating a contrast agent residue function from the acquired time course image data set and the arterial input function; and
    calculating the convolution of the arterial input function and the calculated contrast agent residue function.

* * * * *